United States Patent [19]

Johnson et al.

[11] 4,225,602
[45] Sep. 30, 1980

[54] TETRAHYDROPYRIDINE DERIVATIVE USEFUL FOR INHIBITING BLOOD PLATELET AGGREGATION

[75] Inventors: Malcolm Johnson, Wilmslow; Stuart D. Mills, Macclesfield; Paul J. Phillips, Congleton, all of England

[73] Assignee: Imperial Chemical Industries Limited, London, England

[21] Appl. No.: 26,224

[22] Filed: Apr. 2, 1979

[30] Foreign Application Priority Data

Apr. 12, 1978 [GB] United Kingdom ............... 14322/78

[51] Int. Cl.³ ............................................. A61K 31/44
[52] U.S. Cl. ..................................... 424/263; 546/346
[58] Field of Search ......................... 546/346; 424/263

[56] References Cited
FOREIGN PATENT DOCUMENTS 2101998 8/1972 Fed. Rep. of Germany ........... 546/346

OTHER PUBLICATIONS

Thebault et al., Clinical Pharmacology & Therapeutics, vol. 18 (4) pp. 485–490 (1975).

*Primary Examiner*—Alan L. Rotman
*Attorney, Agent, or Firm*—Cushman, Darby & Cushman

[57] ABSTRACT

The invention concerns the novel amine 1-(2-chlorobenzyl)-1,2,3,6-tetrahydropyridine of the formula:

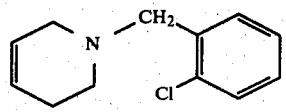

and its pharmaceutically acceptable acid-addition salts, which have useful properties in inhibiting the aggregation of blood platelets, and are of application in the treatment or prophylaxis of thrombosis or occlusive vascular disease. The invention also provides pharmaceutical compositions of, and analogy processes for the manufacture of the amine of formula I, or a salt thereof.

1 Claim, No Drawings

TETRAHYDROPYRIDINE DERIVATIVE USEFUL FOR INHIBITING BLOOD PLATELET AGGREGATION

This invention relates to a novel tetrahydropyridine derivative which inhibits the aggregation of blood platelets.

It is known that the compound ticlopidine of formula:

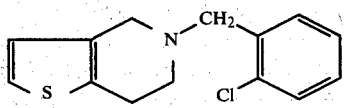

is an inhibitor of the aggregation of blood platelets (Thebault et alia, Clinical Pharmacology and Therapeutics, 1975, 18 (4), 485-490). We have now discovered that the tetrahydropyridine derivative of formula I specified below (or acid-addition salts thereof), which lacks the thiophene ring of ticlopidine, quite unexpectedly also possesses the property of inhibiting the aggregation of blood platelets, and this is the basis for our invention. A related compound, 1-benzyl-1,2,3,6-tetrahydropyridine, is known as a chemical intermediate (Petrow and Stephenson, *J. Pharm. Pharmacol.* 1962, 14, 306-313). The compound of formula I specified below falls within the generic scope of the claims of West German Offenlegungsschrift No. 2,101,998 (addressed to chemical intermediates) but is not specifically disclosed therein, and is therefore believed to be both novel and unobvious over the known art.

According to the invention there is provided the amine 1-(2-chlorobenzyl)-1,2,3,6-tetrahydropyridine of the formula:

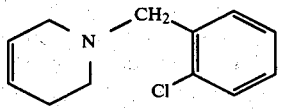

or a pharmaceutically acceptable acid-addition salt thereof.

Particular pharmaceutically acceptable acid-addition salts of the amine of formula I are, for example, salts with inorganic acids, for example with hydrogen chloride, hydrogen bromide, sulphuric acid or phosphoric acid, or salts with organic acids, for example oxalic or citric acid.

The amine of formula I may be manufactured by any general process of organic chemistry known to be applicable to the synthesis of analogous pyridine derivatives. Such process are provided as a further feature of the invention and are illustrated by the following procedures:

(a) Reacting a quaternary salt of the formula:

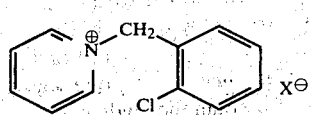

wherein X is an anion, for example a chloride, bromide, iodide, methylsulphonate, toluene-p-sulphonate or sulphate, with a suitable reducing agent.

A suitable reducing agent is, for example an inorganic hydride reducing agent, for example sodium or potassium borohydride, sodium or lithium cyanoborohydride, aluminium hydride or lithium aluminium hydride. The process is conveniently carried out in an inert diluent or solvent, for example tetrahydrofuran when an aluminium hydride is used as reducing agent, or for example a $C_{1-4}$-alkanol such as ethanol when a borohydride or cyanoborohydride is used as reducing agent. The process is preferably carried out at or near room temperature, for example at 15°-35° C., when an inorganic hydride reducing agent is used.

Alternatively, a suitable reducing agent is, for example, a mixture of anhydrous sodium formate in formic acid, and in which case an excess of formic acid may be used as diluent or solvent and the process is preferably carried out at a temperature in the range, for example, 100°-160° C.

The starting materials of formula II may be obtained by reacting pyridine with a 2-chlorobenzyl halide of the formula:

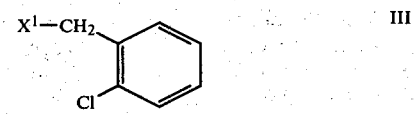

wherein $X^1$ is a chlorine, bromine or iodine atom, conveniently at an elevated temperature, for example at 50°-120° C., and optionally, in the presence of a suitable solvent or diluent, for example toluene, xylene, dioxan, acetonitrile or tetrahydrofuran. When a quaternary salt of formula II wherein $X^{\ominus}$ is other than a halide anion is required, it may be obtained by conventional anion exchange procedures from the corresponding quaternary halide salt.

The salts of formula II are conveniently made and used in situ.

(b) Reacting 1,2,3,6-tetrahydropyridine with a 2-chlorobenzyl halide of formula III [as defined in process (a) hereinbefore].

The process is conveniently carried out in the presence of an inorganic base, for example an alkali metal carbonate, for example potassium carbonate, and is preferably performed in a suitable solvent or diluent, for example a $C_{1-4}$-alkanol, for example ethanol, at a temperature of, for example, 20°-120° C.

(c) Reducing 1-(2-chlorobenzoyl)-1,2,3,6-tetrahydropyridine by reaction with a complex aluminium hydride.

The process is preferably carried out in a suitable solvent or diluent, for example tetrahydrofuran, diethyl ether, di-n-butyl ether or 1,2-dimethoxyethane, and a particularly suitable complex aluminium hydride is, for example, lithium aluminium hydride. The process is conveniently carried out at or near room temperature for example at 15°-33° C.

The starting material may be obtained in an analogous manner and using similar conditions to those described in process (b) for the amine of formula I, except that 2-chlorobenzoyl chloride or bromide and an inert solvent or diluent such as n-butyl acetate, toluene, tetrahydrofuran. pyridine, chloroform or methylene dichloride, are necessary.

(d) Reacting 1,2,3,6-tetrahydropyridine with 2-chlorobenzaldehyde in the presence of a reducing agent.

A particularly suitable reducing agent is, for example, an inorganic hydride, for example sodium or potassium borohydride, lithium aluminium hydride, lithium or sodium cyanoborohydride.

The process is preferably carried out in a solvent or diluent, for example a $C_{1-4}$-alkanol, for example ethanol, and conveniently at, or near, room temperature, for example at 15°-30° C.

Whereafter, when a pharmaceutically acceptable acid-addition salt is required the amine of formula I is reacted with a suitable acid as defined hereinbefore using a conventional procedure.

As stated above, the amine of formula I possesses the property of inhibiting the aggregation of blood platelets. This property may be demonstrated in vivo using standard tests in laboratory animals, for example in the following test in rabbits.

In this test blood samples are taken by a standard open flow technique from the central ear artery of rabbits. The samples are taken into a 3.8% w/v solution of a trisodium citrate as anticoagulant and then centrifuged, first at 150 g., and then at 1000 g., to prepare platelet rich and platelet poor plasma fractions, which are used to calibrate an instrument for measuring light transmittance and thus the amount of platelet aggregation. The extent of platelet aggregation following addition of adenosine 5'-diphosphate (ADP) (final concentration 0.5, 1.0, 2.0, 4.0 or 8.0 $\mu M$) to platelet rich plasma fraction is then determined, and the value of maximum aggregation in response to each concentration of ADP is recorded. The rabbits are then dosed orally with test compound, and arterial blood samples are withdrawn at intervals after dosing. The platelet rich plasma fraction is prepared and ADP is added as above, and the extent of aggregation assessed by measuring the light transmittance of the sample. This value is compared with that obtained from the same rabbit before dosing, so that a measure of the extent of inhibition of ADP induced blood platelet aggregation is obtained. In one such test, the amine 1-(2-chlorobenzyl)-1,2,3,6-tetrahydropyridine showed 65% inhibition of ADP-induced aggregation of blood platelets two hours after an oral dose (as its hydrochloride) of 100 mg./kg. No signs of overt toxicity were produced at the active dose.

Compounds which inhibit the aggregation of blood platelets, for example acetylsalicyclic acid and ticlopidine, have been used in the treatment or prophylaxis of thrombosis or occlusive vascular disease, and it is envisaged that the amine of the present invention will be used in a generally similar manner, and for the same clinical indications.

When used to inhibit the aggregation of blood platelets in warm-blooded animals including man, the amine of formula I may be administered at a daily oral dose in the range 5-30 mg./kg. and preferably in the range 5-10 mg./kg., or an equivalent amount of a pharmaceutically acceptable salt thereof. In man these doses are equivalent to daily oral doses of approximately 0.35-2.1 g. and 0.35-0.7 g. respectively, or an equivalent amount of a pharmaceutically acceptable salt.

The amine of formula I is preferably administered in the form of a pharmaceutical composition, and according to a further feature of the invention there is provided a pharmaceutical composition which comprises the amine of formula I, or a pharmaceutically acceptable salt thereof as defined hereinbefore, together with a pharmaceutically acceptable diluent or carrier. Such a composition is conveniently in a form suitable for oral administration, for example as a tablet, capsule, aqueous or oily solution or suspension, syrup or elixir. Alternatively it may be in a form suitable for parenteral administration by infusion or injection for example, as a sterile injectable solution or suspension, or in a form suitable for rectal administration by suppository.

Such compositions may be obtained by conventional procedures and using conventional excipients. A composition for oral administration should preferably contain from 20-500 mg. of active ingredient per unit dose, a composition for parenteral administration, 0.5-20 mg./ml. of active ingredient, and a composition for rectal administration, 100-500 mg. of active ingredient.

A composition of the invention may also conveniently contain in addition to the amine of formula I one or more agents which can have a beneficial effect on thrombosis or occlusive vascular disease, or on associated conditions, selected from, for example, clofibrate, sulfinpyrazone, dipyridamole or methyl 4-(aminoacetyl)-phenoxyacetate (or a salt thereof).

The invention is illustrated by the following Examples in which (i), yields are by way of example only and are not to be construed as the maximum attainable and (ii), evaporations were carried out in vacuo to dryness where possible, using a rotary evaporator:

EXAMPLE 1

2-Chlorobenzyl chloride (32.2 g.) and pyridine (15.8 g.) were heated together on a steam bath for 1½ hours. After cooling, the solid was triturated with ether and crude 1-(2-chlorobenzyl)-pyridinium chloride (48.0 g.) was separated by filtration. A portion of this quaternary salt (23.9 g.), was stirred in ethanol (150 ml.) and treated portionwise with sodium borohydride (11.4 g.). After further stirring at 25° C. for 16 hours, the mixture was evaporated. Water (100 ml.) was added to the residue and the mixture was then extracted with ether (2×50 ml.). The ether extracts were dried (MgSO$_4$) and then evaporated to give an oil which was distilled at 0.5 mm.Hg. The fractions boiling over the temperature range 91° to 105° C. were combined to give an oil (9.4 g.). This oil was dissolved in ether (50 ml.) and the solution obtained was treated with a slight excess of ethereal hydrogen chloride to give 1-(2-chlorobenzyl)-1,2,3,6-tetrahydropyridine hydrochloride (7.35 g.), m.p. 213°-215° C. (sealed tube) (after crystallisation from ethanol/ethyl acetate).

EXAMPLE 2

A solution of 1,2,3,6-tetrahydropyridine (8.3 g.) in ethanol (100 ml.) was treated with 2-chlorobenzyl chloride (16.1 g.) and potassium carbonate (15.2 g.). The mixture was then refluxed for 2 hours, cooled and evaporated. Water (100 ml.) was added to the residue and the oily product was extracted with ether (100 ml.). The ether extract was washed with water (100 ml.), dried (MgSO$_4$) and evaporated. The oily residue was treated with a slight excess of methanolic hydrogen chloride, and the mixture evaporated. The solid obtained was stirred with acetone, separated by filtration and recrystallized from ethanol-ethyl acetate to give 1-(2-chlorobenzyl)-1,2,3,6-tetrahydropyridine hydrochloride (12.7 g.), m.p. 213°-215° C. (sealed tube).

EXAMPLE 3

(Note: all parts are by weight)

A mixture of micro-crystalline cellulose (196 parts) and finely divided 1-(2-chlorobenzyl)-1,2,3,6-tetrahydropyridine hydrochloride (200 parts) was sieved through a 30 mesh screen. Magnesium stearate (60 mesh particle size) (4 parts) was then added and, after thorough mixing, the mixture was compressed into tablets weighing 400 mg. and containing 20 mg. of active ingredient, which may be administered to man for therapeutic purposes.

Using a similar procedure tablets containing 20, 50, 100 and 400 mg. of active ingredient may be obtained.

What is claimed is:

1. A method for inhibiting the aggregation of blood platelets in a warm-blooded animal requiring such treatment, which comprises administering to said animal an effective amount of 1-(2-chlorobenzyl)-1,2,3,6-tetrahydropyridine, or a pharmaceutically acceptable acid-addition salt thereof.

* * * * *